United States Patent [19]

Sasse et al.

[11] Patent Number: 4,797,146

[45] Date of Patent: * Jan. 10, 1989

[54] HERBICIDAL 2-[4-SUBSTITUTED CARBOXYAMINO-PHENYL MERCAPTO)]-SUBSITUTED PYRIMIDINES

[75] Inventors: Klaus Sasse, Bergisch Gladbach; Hermann Hagemann; Hans-Joachim Santel, both of Leverkusen; Robert R. Schmidt, Bergisch Gladbach, all of Fed. Rep. of Germany

[73] Assignee: Bayer Aktiengesellschaft, Leverkusen, Fed. Rep. of Germany

[*] Notice: The portion of the term of this patent subsequent to Dec. 9, 2003 has been disclaimed.

[21] Appl. No.: 937,940

[22] Filed: Dec. 4, 1986

[30] Foreign Application Priority Data

Dec. 13, 1985 [DE] Fed. Rep. of Germany ....... 3544208

[51] Int. Cl.$^4$ ............... C07D 239/02; A01N 43/48
[52] U.S. Cl. ........................ 71/92; 544/316; 544/318
[58] Field of Search .................. 546/316, 318; 71/92

[56] References Cited

U.S. PATENT DOCUMENTS 4,627,871 5/1985 Sasse et al. .................. 544/316

FOREIGN PATENT DOCUMENTS 0168608 1/1986 European Pat. Off. ......... 544/316
2501648 7/1975 Fed. Rep. of Germany ..... 546/290
109170 10/1974 German Democratic Rep. .................. 544/316

OTHER PUBLICATIONS

Pp. 311–314–Springer Verlag, Berlin (1970).
Japan 55/122,763–Herbicidal Pyridly:oxy—Acid.
Japan 56/029,576–Pyridazinyl:oxy—Acid.
Japan 56/123,970–Herbicide Compan.for Soybean, Wheat—Components(s).
Japan 9,474/1967–Herbicidal Composition Comprises as Active—Phenoxypyrimidine.

Primary Examiner—Mary C. Lee
Assistant Examiner—Zinna Northington
Attorney, Agent, or Firm—Sprung Horn Kramer & Woods

[57] ABSTRACT

Herbicidally, fungicidally and insecticidally active pyrimidylmercapto-acylanilides of the formula

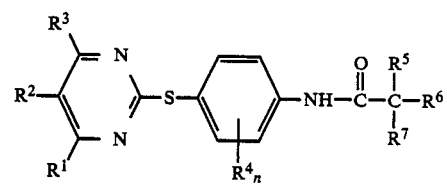

in which
$R^1$ represents methyl or ethyl,
$R^2$ represents halogen, methyl or ethyl,
$R^3$ represents hydrogen or methyl,
$R^4$ represents hydrogen, methyl or methoxy,
n represents 0, 1 or 2,
$R^5$ represents hydrogen, halogen, cyano, optionally substituted alkyl having 1 to 6 carbon atoms, optionally substituted aryl, optionally substituted aralkyl or the $-OR^8$ or $-SO_m-R^8$ radicals, where
$R^8$ represents optionally substituted alkyl having 1 to 6 carbon atoms or optionally substituted aryl and
m represents 0, 1 or 2, and
$R^6$ and $R^7$, independently of one another, represent halogen or optionally substituted alkyl having 1 to 6 carbon atoms or
$R^5$ and $R^6$, together with the neighboring carbon atom, represent an optionally substituted, saturated or unsaturated ring, which has 3 to 8 ring members and which can also contain oxygen and sulphur atoms in addition to carbon atoms, or
$R^6$ and $R^7$, together with the neighboring carbon atom, represent an optionally substituted saturated or unsaturated ring which has 3 to 8 ring carbon atoms.

12 Claims, No Drawings

HERBICIDAL 2-[4-SUBSTITUTED CARBOXYAMINO-PHENYL MERCAPTO)]-SUBSITUTED PYRIMIDINES

The present invention relates to new pyrimidylmercapto-acylaniides, several processes for their preparation and their use as herbicides.

It is already known that certain carboxanilides have herbicidal properties (cf. R. Wegler "Chemie der Pflanzenschutz- und Schädlingsbekämpfungsmittel [Chemistry of plant protection agents and pesticides]" Vol. 2, pages 311–314, Springer-Verlag, Berlin 1970). Thus, for example, propion-3,4-dichloroanilide can be employed for combating weeds. The action of this compound is good, but some weeds are not always fully covered when low amounts are applied. In addition, the selectivity also leaves something to be desired in some cases.

Furthermore, it is known that numerous 2-pyrimidinyl ethers and thioethers are suitable as herbicides (cf. Japanese Published Specification No. 9,474/1967, U.S. Pat. No. 3,126,271 and U.S. Pat. No. 3,250,775). For example, 2-phenoxy-4,6-dimethylpyrimidine and 2-(4-chlorobenzylmercapto)-4,6-dimethylpyrimidine can be used to combat weeds. However, the herbicidal potency of these substances is not always adequate.

Furthermore, it is known that lower aryl derivatives of 4-pyridyloxy-(or thio)-anilines possess herbicidal properties (cf. DE-OS No. (German Published Specification) 2,501,648, Japanese Published Specification No. 55/122,763 and Japanese Published Specification No. 56/123,970). In addition, herbicidally active acyl derivatives of 4-pyrimidyloxy-anilines are also known which are substituted in the 5-position of the pyrimidyl radical by halogen or trifluoromethyl, but do not contain substituents in the 4 and 6 positions (cf. Japanese Published Specification No. 56/029,576). The activity of these substances is, however, also not always adequate for practical purposes.

New pyrimidylmercapto-acylanilides of the formula (I),

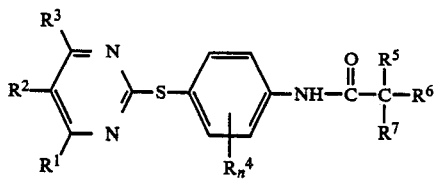

in which
- $R^1$ represents methyl or ethyl,
- $R^2$ represents halogen, methyl or ethyl,
- $R^3$ represents hydrogen or methyl,
- $R^4$ represents halogen, methyl or methoxy,
- n represents 0, 1 or 2,
- $R^5$ represents hydrogen, halogen, cyano, optionally substituted alkyl having 1 to 6 carbon atoms, optionally substituted aryl, optionally substituted aralkyl or —O—$R^8$ or —SO$_m$—$R^8$ radicals, where $R^8$ represents optionally substituted alkyl having 1 to 6 carbon atoms or optionally substituted aryl and m represents 0, 1 or 2, and
- $R^6$ and $R^7$, independently of one another, represent halogen or optionally substituted alkyl having 1 to 6 carbon atoms or
- $R^5$ and $R^6$, together with the neighboring carbon atom, represent an optionally substituted, saturated or unsaturated ring, which has 3 to 8 ring members and which can also contain oxygen and sulphur atoms in addition to carbon atoms, or
- $R^6$ and $R^7$, together with the neighboring carbon atom, represent an optionally substituted saturated or unsaturated ring which has 3 to 8 ring carbon atoms, have now been found.

It has furthermore been found that pyrimidylmercapto-acylanilides of the formula (I) are obtained when
(a) aniline derivatives of the formula (II),

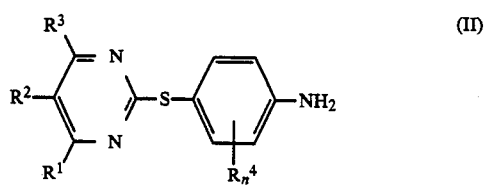

in which
$R^1$, $R^2$, $R^3$, $R^4$ and n have the abovementioned meaning,
are
(α) reacted with acid halides of the formula (IIIa),

in which
$R^5$, $R^6$ and $R^7$ have the abovementioned meaning, and
Y represents halogen,
if appropriate in the presence of a diluent and if appropriate in the presence of an acid binder, or
(β) reacted with symmetrical carboxylic acid anhydrides of the formula (IIIb),

in which
$R^5$, $R^6$ and $R^7$ have the abovementioned meaning, if appropriate in the presence of a diluent, or
(γ) reacted with asymmetrical acid anhydrides of the formula (IIIc),

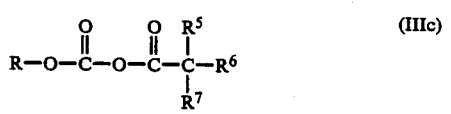

in which
$R^5$, $R^6$ and $R^7$ have the abovementioned meaning and
R represents alkyl having 1 to 4 carbon atoms or phenyl,
if appropriate in the presence of a diluent, or
(δ) reacted with compounds of the formula (IIId),

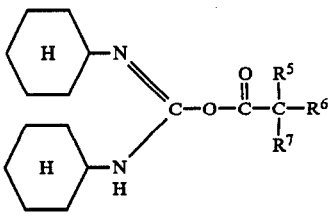

(IIId)

in which
R[5], R[6] and R[7] have the abovementioned meaning, if appropriate in the presence of a diluent, or when
(b) pyrimidine derivatives of the formula (IV),

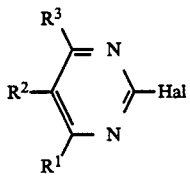

(IV)

in which
R[1], R[2] and R[3] have the abovementioned meaning and Hal represents halogen,
are reacted with acylaniline derivatives of the formula (V),

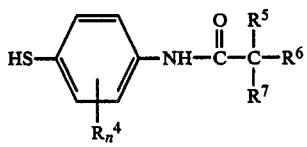

(V)

in which
R[4], R[5], R[6], R[7] and n have the abovementioned meaning,
in the presence of a diluent.

Finally, it has been found that the new pyrimidylmercapto-acylanilides of the formula (I) distinguish themselves by excellent herbicidal activity.

Surprisingly, the pyrimidylmercapto-acylanilides of the formula (I) according to the invention have significantly better herbicidal properties than the constitutionally most similar substances which were previously known. Thus, the pyrimidylmercapto-acylanilides of the formula (I) according to the invention can be used significantly better for combating weeds than 2-phenoxy-4,6-dimethylpyrimidine, which is a structurally similar, previously known active compound with a similar mode of action.

The pyrimidylmercapto-acylanilides according to the invention are generally defined by the formula (I). Compounds of the formula (I) in which
$R^1$ represents methyl or ethyl,
$R^2$ represents fluorine, chlorine, bromine, methyl or ethyl,
$R^3$ represents hydrogen or methyl,
$R^4$ represents fluorine, chlorine, bromine, methyl or methoxy,
n represents 0 or 1,
$R^5$ represents hydrogen, fluorine, chlorine, bromine, cyano, alkyl, having 1 to 4 carbon atoms, which is optionally substituted by fluorine, chlorine, bromine and/or alkoxy having 1 to 4 carbon atoms, phenyl, which is optionally substituted by fluorine, chlorine, bromine, trifluoromethyl, methoxy and/or methyl, benzyl which is optionally substituted by fluorine, chlorine, bromine, trifluoromethyl, methoxy and/or methyl or represents the $—OR^8$ or $—SO_m—R^8$ radicals, where
$R^8$ represents alkyl, having 1 to 4 carbon atoms, which is optionally substituted by fluorine, chlorine and/or bromine, or phenyl which is optionally substituted by fluorine, chlorine, bromine and/or alkyl having 1 to 4 carbon atoms and m represents 0, 1 or 2,
$R^6$ and $R^7$, independently of one another, represent fluorine, chlorine, bromine or alkyl, having 1 to 4 carbon atoms, which is optionally substituted by fluorine, chlorine and/or bromine or
$R^5$ and $R^6$, together with the neighboring carbon atom, represent a saturated or unsaturated ring, which has 3 to 7 ring atoms and which can also contain oxygen and sulphur atoms as ring members in addition to carbon atoms and which is optionally substituted by fluorine, chlorine and/or alkyl having 1 to 4 carbon atoms or
$R^6$ and $R^7$, together with the neighboring carbon atom, represent a saturated or unsaturated ring, which has 3 to 7 ring atoms and which is optionally substituted by fluorine, chlorine and/or alkyl having 1 to 4 carbon atoms, are preferred. A particularly preferred group of substances according to the invention are those substituted carboxanilides of the formula (I)
in which
$R^1$ represents methyl or ethyl,
$R^2$ represents fluorine, chlorine, methyl or ethyl,
$R^3$ represents hydrogen or methyl,
$R^4$ represents fluorine, chlorine, methyl or methoxy,
n represents 0 or 1,
$R^5$ represents fluorine, chlorine, bromine, cyano, alkyl, having 1 to 4 carbon atoms, which is optionally singly or quintuply substituted by fluorine, chlorine, methoxy and/or ethoxy, phenyl, which is optionally singly to triply substituted by fluorine, chlorine and/or methyl, benzyl which is optionally singly to quintuply substituted by fluorine, chlorine and/or methyl or the $—OR^8$ or $—SO_m—R^8$ radicals, where $R^8$ represents alkyl, having 1 to 4 carbon atoms, which is optionally singly to quintuply substituted by fluorine and/or chlorine, or represents phenyl which is optionally singly to quintuply substituted by fluorine, chlorine and/or alkyl having 1 to 4 carbon atoms and m represents 0, 1 or 2,
$R^6$ and $R^7$, independently of one another, represent fluorine, chlorine or alkyl, having 1 to 4 carbon atoms, which is optionally singly to quintuply substituted by fluorine and/or chlorine or
$R^5$ and $R^6$, together with the neighboring carbon atom, represent a saturated or unsaturated ring, which has 3 to 7 ring atoms, which can also contain oxygen and sulphur atoms as ring members in addition to carbon atoms, and which is optionally singly to quintuply identically or differently substituted by fluorine, chlorine, methyl, ethyl, n-propyl, isopropyl, n-butyl, iso-butyl, sec.-butyl and tert.-butyl, or
$R^6$ and $R^7$, together with the neighboring carbon atom, represent a saturated or unsaturated ring which has 3 to 7 ring atoms and which is optionally singly to quintuply identically or differently substituted by fluorine, chlorine, methyl, ethyl, n-propyl, iso-propyl, n-butyl, iso-butyl, sec.-butyl or tert.-butyl.

The substances listed in Table 1 below may be mentioned as examples of substituted carboxanilides of the formula (I).

TABLE 1

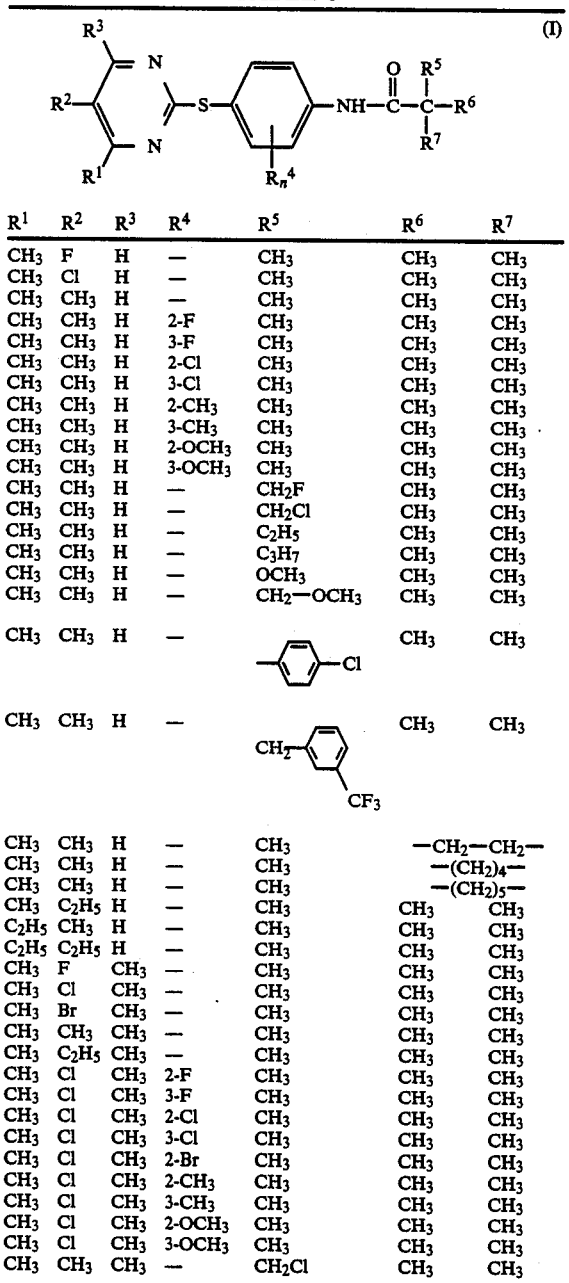

| $R^1$ | $R^2$ | $R^3$ | $R^4$ | $R^5$ | $R^6$ | $R^7$ |
|---|---|---|---|---|---|---|
| CH$_3$ | F | H | — | CH$_3$ | CH$_3$ | CH$_3$ |
| CH$_3$ | Cl | H | — | CH$_3$ | CH$_3$ | CH$_3$ |
| CH$_3$ | CH$_3$ | H | — | CH$_3$ | CH$_3$ | CH$_3$ |
| CH$_3$ | CH$_3$ | H | 2-F | CH$_3$ | CH$_3$ | CH$_3$ |
| CH$_3$ | CH$_3$ | H | 3-F | CH$_3$ | CH$_3$ | CH$_3$ |
| CH$_3$ | CH$_3$ | H | 2-Cl | CH$_3$ | CH$_3$ | CH$_3$ |
| CH$_3$ | CH$_3$ | H | 3-Cl | CH$_3$ | CH$_3$ | CH$_3$ |
| CH$_3$ | CH$_3$ | H | 2-CH$_3$ | CH$_3$ | CH$_3$ | CH$_3$ |
| CH$_3$ | CH$_3$ | H | 3-CH$_3$ | CH$_3$ | CH$_3$ | CH$_3$ |
| CH$_3$ | CH$_3$ | H | 2-OCH$_3$ | CH$_3$ | CH$_3$ | CH$_3$ |
| CH$_3$ | CH$_3$ | H | 3-OCH$_3$ | CH$_3$ | CH$_3$ | CH$_3$ |
| CH$_3$ | CH$_3$ | H | — | CH$_2$F | CH$_3$ | CH$_3$ |
| CH$_3$ | CH$_3$ | H | — | CH$_2$Cl | CH$_3$ | CH$_3$ |
| CH$_3$ | CH$_3$ | H | — | C$_2$H$_5$ | CH$_3$ | CH$_3$ |
| CH$_3$ | CH$_3$ | H | — | C$_3$H$_7$ | CH$_3$ | CH$_3$ |
| CH$_3$ | CH$_3$ | H | — | OCH$_3$ | CH$_3$ | CH$_3$ |
| CH$_3$ | CH$_3$ | H | — | CH$_2$—OCH$_3$ | CH$_3$ | CH$_3$ |
| CH$_3$ | CH$_3$ | H | — | —⟨C$_6$H$_4$⟩—Cl | CH$_3$ | CH$_3$ |
| CH$_3$ | CH$_3$ | H | — | —CH$_2$⟨C$_6$H$_4$⟩—CF$_3$ | CH$_3$ | CH$_3$ |
| CH$_3$ | CH$_3$ | H | — | CH$_3$ | —CH$_2$—CH$_2$— | |
| CH$_3$ | CH$_3$ | H | — | CH$_3$ | —(CH$_2$)$_4$— | |
| CH$_3$ | CH$_3$ | H | — | CH$_3$ | —(CH$_2$)$_5$— | |
| CH$_3$ | C$_2$H$_5$ | H | — | CH$_3$ | CH$_3$ | CH$_3$ |
| C$_2$H$_5$ | CH$_3$ | H | — | CH$_3$ | CH$_3$ | CH$_3$ |
| C$_2$H$_5$ | C$_2$H$_5$ | H | — | CH$_3$ | CH$_3$ | CH$_3$ |
| CH$_3$ | F | CH$_3$ | — | CH$_3$ | CH$_3$ | CH$_3$ |
| CH$_3$ | Cl | CH$_3$ | — | CH$_3$ | CH$_3$ | CH$_3$ |
| CH$_3$ | Br | CH$_3$ | — | CH$_3$ | CH$_3$ | CH$_3$ |
| CH$_3$ | CH$_3$ | CH$_3$ | — | CH$_3$ | CH$_3$ | CH$_3$ |
| CH$_3$ | C$_2$H$_5$ | CH$_3$ | — | CH$_3$ | CH$_3$ | CH$_3$ |
| CH$_3$ | Cl | CH$_3$ | 2-F | CH$_3$ | CH$_3$ | CH$_3$ |
| CH$_3$ | Cl | CH$_3$ | 3-F | CH$_3$ | CH$_3$ | CH$_3$ |
| CH$_3$ | Cl | CH$_3$ | 2-Cl | CH$_3$ | CH$_3$ | CH$_3$ |
| CH$_3$ | Cl | CH$_3$ | 3-Cl | CH$_3$ | CH$_3$ | CH$_3$ |
| CH$_3$ | Cl | CH$_3$ | 2-Br | CH$_3$ | CH$_3$ | CH$_3$ |
| CH$_3$ | Cl | CH$_3$ | 2-CH$_3$ | CH$_3$ | CH$_3$ | CH$_3$ |
| CH$_3$ | Cl | CH$_3$ | 3-CH$_3$ | CH$_3$ | CH$_3$ | CH$_3$ |
| CH$_3$ | Cl | CH$_3$ | 2-OCH$_3$ | CH$_3$ | CH$_3$ | CH$_3$ |
| CH$_3$ | Cl | CH$_3$ | 3-OCH$_3$ | CH$_3$ | CH$_3$ | CH$_3$ |
| CH$_3$ | CH$_3$ | CH$_3$ | — | CH$_2$Cl | CH$_3$ | CH$_3$ |

TABLE 1-continued

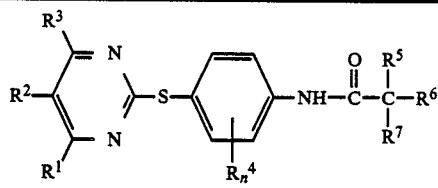

| $R^1$ | $R^2$ | $R^3$ | $R^4$ | $R^5$ | $R^6$ | $R^7$ |
|---|---|---|---|---|---|---|
| CH$_3$ | CH$_3$ | CH$_3$ | — | CH$_2$F | CH$_3$ | CH$_3$ |
| CH$_3$ | CH$_3$ | CH$_3$ | — | H | CH$_3$ | CH$_3$ |
| CH$_3$ | CH$_3$ | CH$_3$ | — | C$_2$H$_5$ | CH$_3$ | CH$_3$ |
| CH$_3$ | CH$_3$ | CH$_3$ | — | C$_3$H$_7$ | CH$_3$ | CH$_3$ |
| CH$_3$ | CH$_3$ | CH$_3$ | — | OCH$_3$ | CH$_3$ | CH$_3$ |
| CH$_3$ | CH$_3$ | CH$_3$ | — | CH$_2$—OCH$_3$ | CH$_3$ | CH$_3$ |
| CH$_3$ | CH$_3$ | CH$_3$ | — | SCH$_3$ | CH$_3$ | CH$_3$ |
| CH$_3$ | CH$_3$ | CH$_3$ | — | —⟨C$_6$H$_5$⟩ | CH$_3$ | CH$_3$ |
| CH$_3$ | CH$_3$ | CH$_3$ | — | —CH$_2$⟨C$_6$H$_4$⟩—Cl | CH$_3$ | CH$_3$ |
| CH$_3$ | CH$_3$ | CH$_3$ | — | CH$_3$ | —CH$_2$—CH$_2$— | |
| CH$_3$ | CH$_3$ | CH$_3$ | — | CH$_3$ | —(CH$_2$)$_4$— | |
| CH$_3$ | CH$_3$ | CH$_3$ | — | CH$_3$ | —(CH$_2$)$_5$— | |

If 4-(5-chloro-4,6-dimethyl-pyrimidyl-2-mercapto)-aniline and pivalic chloride are used as starting materials, then the course of the process (a, version α) according to the invention can be described by means of the following scheme:

If 4-(4,5-dimethyl-pyrimidyl-2-mercapto)-aniline and isobutyric anhydride are used as starting materials, then the course of the process (a, version β) according to the invention can be described by means of the following scheme:

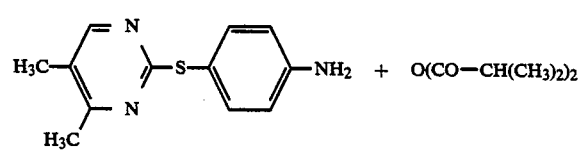

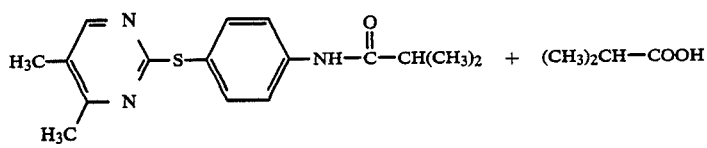

If 4-(4,5,6-trimethyl-pyrimidyl-2-mercapto)-aniline and α-methoxy-isobutyric carbonic anhydride ethyl ester are used as starting materials, then the course of the process (a, version γ) according to the invention can be described by means of the following scheme:

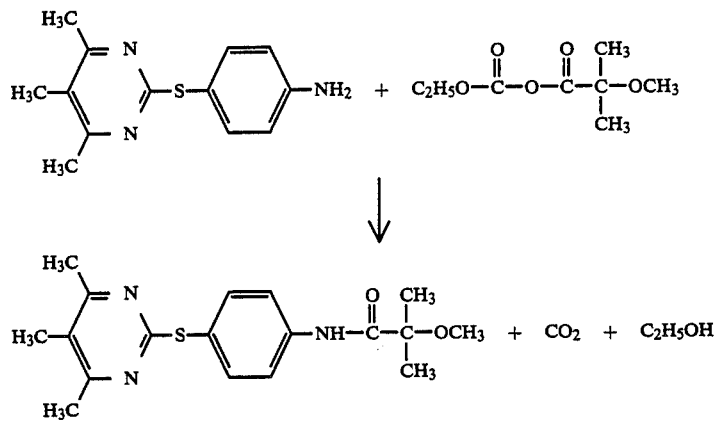

If 4-(4-methyl-5-fluoro-pyrimidyl-2-mercapto)-aniline and O-pivaloyloxy-dicyclohexyl-isourea are used as starting materials, then the course of the process (a, version δ) according to the invention can be described by means of the following scheme:

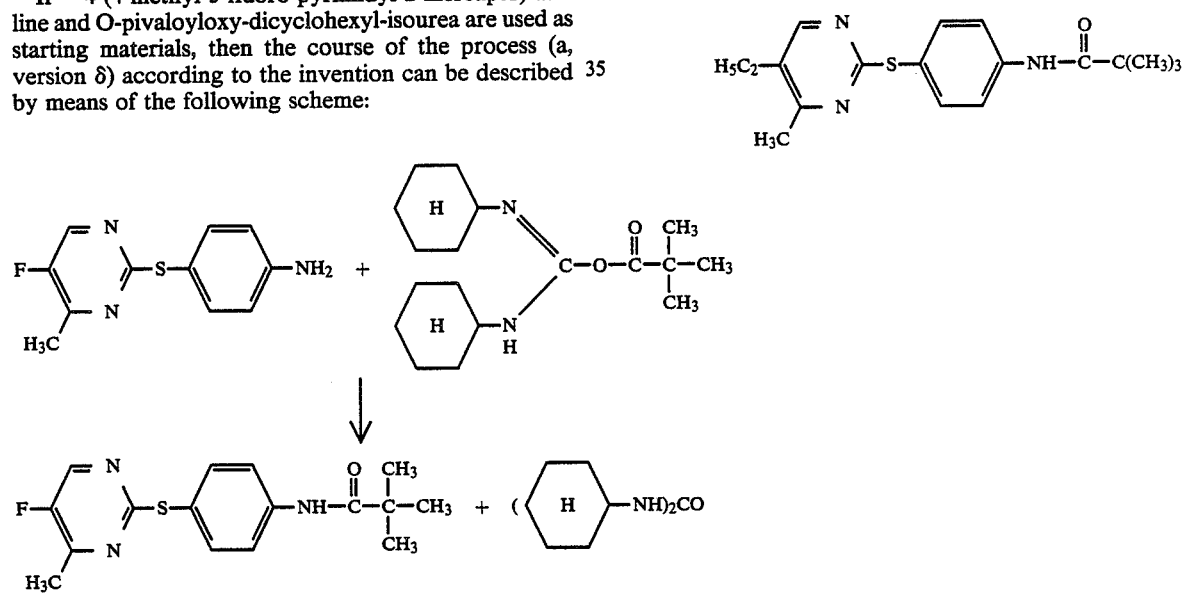

If 2-chloro-4-methyl-5-ethyl-pyrimidine and 4-pivaloylamino-thiophenol are used as starting materials, then the course of the process (b) according to the invention can be described by means of the following formula scheme:

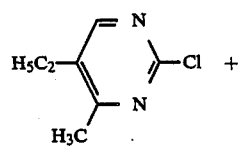

The aniline derivatives required as starting materials in the process (a) according to the invention are generally defined by the formula (II). In this formula, $R^1$, $R^2$, $R^3$, $R^4$ and n preferably have the meanings which have already been mentioned in connection with the description of the substances of the formula (I) according to the invention as being preferable for these radicals and this index respectively.

Some of the aniline derivatives of the formula (II) are known. They can be prepared by (c) reacting pyrimidine derivatives of the formula (IV),

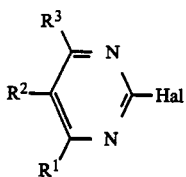

in which
R$^1$, R$^2$ and R$^3$ have the abovementioned meaning and Hal represents halogen, with 4-amino-thiophenol of the formula (VI),

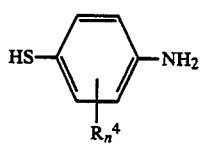

in which
R$^4$ and n have the abovementioned meaning, in the presence of an acid binder and if appropriate in the presence of a diluent, or (d) by reducing 2-(4-nitro-thiophenoxy)-pyrimidine derivatives of the formula (VII),

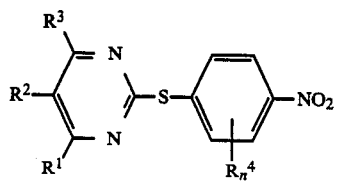

in which
R$^1$, R$^2$, R$^3$, R$^4$ and n have the abovementioned meaning,
by conventional methods, if appropriate in the presence of a diluent.

The pyrimidine derivatives required as starting materials in the above process (c) are defined by the formula (IV). In this formula, R$^1$, R$^2$ and R$^3$ preferably have the definitions which have already been mentioned in connection with the description of the substances of the formula (I) according to the invention as being preferable for these radicals. Hal preferably represents fluorine, chlorine or bromine.

Examples of pyrimidine derivatives of the formula (IV) which may be mentioned are:
2,5-Difluoro-4-methyl-pyrimidine
2,5-Dichloro-4-methyl-pyrimidine
2-Chloro-4,5-dimethyl-pyrimidine
2-Chloro-4-methyl-5-ethyl-pyrimidine
2-Chloro-4-ethyl-5-methyl-pyrimidine
2-Chloro-4,5-diethyl-pyrimidine
2,5-Difluoro-4,6-dimethyl-pyrimidine
2,5-Dichloro-4,6-dimethyl-pyrimidine
2-Chloro-5-bromo-4,6-dimethyl-pyrimidine
2-Chloro-4,5,6-trimethyl-pyrimidine
2-Chloro-4,6-dimethyl-5-ethyl-pyrimidine.

The pyrimidine derivatives of the formula (IV) are known or can be prepared in a simple fashion according to methods which are known in principle. Thus, pyrimidine derivatives of the formula (IV) are obtained, for example, by reacting 2-hydroxy-pyrimidine derivatives (dihydro-pyrimidone-2 derivatives) with inorganic acid halides, such as, for example, phosphoroxy chloride or phosphorus pentachloride, or alternatively by reacting appropriate 2-amino-pyrimidine derivatives with nitrous acid in the presence of hydrohalic acids.

The 4-amino-thiophenols which are further required as starting materials in the process (c) are defined by the formula (VI). In this formula, R$^4$ and n preferably have the meanings which have already been mentioned in connection with the description of the substances of the formula (I) according to the invention as being preferable for these radicals and for this index respectively.

Examples of 4-amino-thiophenols of the formula (VI) which may be mentioned are:
4-Amino-thiophenol
2-Fluoro-4-amino-thiophenol
3-Fluoro-4-amino-thiophenol
2-Chloro-4-amino-thiophenol
3-Chloro-4-amino-thiophenol
2-Bromo-4-amino-thiophenol
3-Bromo-4-amino-thiophenol
2-Methyl-4-amino-thiophenol
3-Methyl-4-amino-thiophenol
2-Methoxy-4-amino-thiophenol
3-Methoxy-4-amino-thiophenol.

The 4-amino-thiophenols of the formula (VI) are known or can be prepared in a simple fashion according to methods which are known in principle.

All acid acceptors which can conventionally be used for this reactions of this type can be used as acid binders when process (c) is carried out. Alkali metal and alkaline earth metal oxides, hydroxides and carbonates, such as sodium hyroxide, potassium hydroxide, calcium oxide, sodium carbonate and potassium carbonate, furthermore alkali metal alcoholates, amides and hydrides, such as, for example, sodium methylate, sodium ethylate, potassium tert.-butylate, sodium amide and sodium hydride, can preferably be used.

All conventional inert organic solvents can be used as diluents when the process (c) is carried out. Hydrocarbons, such as benzine, toluene and xylene, furthermore ethers, such as dioxane, glycol dimethyl ether and diglycol dimethyl ether, in addition nitriles, such as acetonitrile, and also strongly polar solvents, such as dimethyl sulphoxide, sulpholane and dimethylformamide, are preferably suitable.

The reaction temperatures can be varied within a relatively wide range when the process (c) is carried out. In general, the process is carried out at temperatures between 0° C. and 200° C., preferably between 50° C. and 150° C.

The reaction according to the process (c) is, in general, carried out under standard pressure.

The starting materials of the formulae (IV) and (VI) are, in general, employed in approximately equimolar amounts when the process (c) is carried out. It is, however, also possible to use one or other component in a relatively large excess. Work-up according to conventional methods.

The 2-(4-nitro-thiophenoxy)-pyrimidine derivatives which are required as starting materials in the process (d) are defined by the formula (VII). In this formula, R$^1$, R$^2$, R$^3$, R$^4$ and n preferably have the meanings which have already been mentioned in connection with the description of the substances of the formula (I) according to the invention as being preferable for these radicals and for this index respectively.

The compounds of the formula (VII) are known or can be prepared in a simple fashion according to methods which are known in principle. Thus, compounds of the formula (VII) are obtained, for example, by reacting pyrimidine derivatives of the formula (IV),

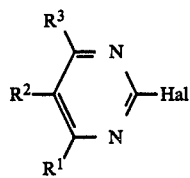

in which
R¹, R², R³ and Hal have the abovementioned meaning,
with 4-nitro-thiophenols of the formula (IX),

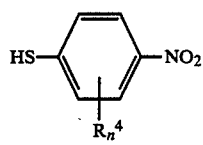

in which
R⁴ and n have the abovementioned meaning, in the presence of an acid binder and, if appropriate, in the presence of a diluent, at temperatures between 0° C. and 100° C., preferably between 50° C. and 150° C. Suitable acid binders and diluents in this case are preferably the substances which have already been mentioned in connection with the process (c) as being acid acceptors and solvents which can preferably be used.

All the substances which are conventionally employed for the reduction of aromatic nitro compounds are suitable as reducing agents in the process (d). Elementary metals, such as iron, zinc and tin, furthermore metal compounds in low valency states, such as iron(II) and tin(II) salts, and, in addition, non-metallic compounds in low valency states, such as, for example, salts of hydrogen sulphide, alkali metal sulphites and alkali metal dithionites, can preferably be used. Besides this, the reduction can also be carried out by catalytic hydrogenation using hydrogen in the presence of a catalyst, such as, for example, Raney nickel.

All conventional organic solvents which are suitable for reductions of this type are suitable as diluents in the process (d). The reaction temperatures can be varied within a relatively wide range. They correspond to the temperatures which are used in analogous reactions.

The reduction according to the process (d) is carried out, and the reaction mixture produced is worked up, according to conventional methods.

The acid halides which are required as reaction components in the process (a, version α) according to the invention are clearly defined of the formula (IIIa). In this formula, $R^5$, $R^6$ and $R^7$ preferably have the meanings which have already been mentioned in connection with the description of the substances of the formula (I) according to the invention as being preferable for these radicals. Y preferably represents fluorine, chlorine and bromine.

The chlorides of the following acids may be mentioned as examples of acid halides of the formula (IIIa):
Trifluoroacetic acid
Trifluoroacetic acid
α,α-Dichloropropionic acid
Isobutyric acid
α-Chloro-isobutyric acid
α-Bromo-isobutyric acid
α-Methoxy-isobutyric acid
α-Phenoxy-isobutyric acid
α-(4-Chloro-phenoxy)-isobutyric acid
α-(2-Methyl-4-chloro-phenoxy)-isobutyric acid
α-Methylmercapto-isobutyric acid
α-Methylsulphonyl-isobutyric acid
α-Methyl-butyric acid
Pivalic acid
β-Fluoro-pivalic acid
β-Chloro-pivalic acid
β,β'-Difluoro-pivalic acid
β,β'-Dichloro-pivalic acid
β,β'β''-Trifluoro-pivalic acid
β,β',β''-Trichloro-pivalic acid
α,α-Dimethyl-valeric acid
α-Methyl-α-ethyl-butyric acid
α,α-Dimethyl-phenylacetic acid
α,α-Dimethyl-(4-chloro-phenyl)-acetic acid
α,α-Dimethyl-(3,4-dichloro-phenyl)-acetic acid
α,α-Dimethyl-(3-trifluoromethyl-phenyl)-acetic acid
α-Benzyl-isobutyric acid
α-(4-Chloro-benzyl)-isobutyric acid
α-(4-Methoxy-benzyl)-isobutyric acid
Cyclopropanoic acid
1-Methyl-cyclopropanoic acid
2,2-Dichloro-1-methyl-cyclopropanoic acid
Cyclopentanoic acid
1-Methyl-cyclopentanoic acid
Cyclohexanoic acid
1-Methyl-cyclohexanoic acid
1-Methyl-4-isopropyl-cyclohexanoic acid.

The acid halides of the formula (IIIa) are known or can be prepared in a simple fashion according to methods which are known in principle.

All solvents which are inert towards acid halides can be employed as diluents in the process (a, version α) according to the invention. Hydrocarbons, such as benzine, benzene, toluene, xylene and tetralin, furthermore halohydrocarbons, such as methylene chloride, chloroform, carbon tetrachloride, chlorobenzene and o-dichlorobenzene, in addition ketones, such as acetone and methyl isopropyl ketone, moreover ethers, such as diethyl ether, tetrahydrofuran and dioxane, additionally carboxylic acid esters, such as ethyl acetate, and also strongly polar solvents, such as dimethyl sulphoxide and sulpholane, can preferably be used. If the stability of the acid halide to hydrolysis allows it, the reaction can also be carried out in the presence of water.

All conventional acid acceptors are suitable as acid binders in the reaction according to the process (a, version α) according to the invention. Tertiary amines, such as triethylamine, pyridine and N,N-dimethyl-aniline, furthermore alkaline earth metal oxides, such as magnesium oxide and calcium oxide, in addition alkali metal and alkaline earth metal carbonates, such as sodium carbonate, potassium carbonate and calcium carbonate, can preferably be used. It is also possible to use the respective aniline derivatives of the formula (II) simultaneously as acid binders. For this purpose, the aniline compound concerned must then be employed at least in an amount such that the liberated hydrogen halide can be bound.

The reaction temperatures can be varied within a relatively wide range when the process (a, version α) according to the invention is carried out. If the process is carried out without solvent and acid binder, then, in general, the components are initially allowed to react at temperatures between −20° C. and +20° C. and are then heated to temperatures between 70° and 200° C. If the process is carried out in the presence of a diluent and an acid binder, then the reaction temperatures are, in general, between −20° C. and +100° C., preferably between 0° C. and 50° C.

The process (a, version α) according to the invention is, in general, carried out under standard pressure.

The starting materials of the formulae (II) and (IIIa) are, in general, used in approximately equivalent amounts when the process (a, version α) according to the invention is carried out. However, it is also possible to employ either component in a relatively large excess.

Work-up occurs according to conventional methods. In general, the precipitated salts are removed and the reaction mixture remaining is concentrated by removal of the diluent. If the process is carried out in the presence of water or water-miscible solvents, then a procedure can also be adopted in which the reaction mixture is diluted with water, the mixture produced is filtered off under suction or extracted using an organic solvent which is sparingly miscible with water, the organic layer is washed and concentrated, and the residue which remains is, if appropriate, subjected to conventional purification processes.

The symmetrical carboxylic acid anhydrides which are required as reaction components in the process (a, version α) according to the invention are clearly defined by the formula (IIIb). In this formula, $R^5$, $R^6$ and $R^7$ preferably have the meanings which have already been mentioned in connection with the description of the substances of the formula (I) according to the invention as being preferable for these radicals.

The symmetrical carboxylic acid anhydrides of the formula (IIIb) are known or can be prepared in a simple fashion according to methods which are known in principle.

The diluents which are also preferably suitable in the process (a, version α) can be preferably used as diluents when the process (a, version β) according to the invention is carried out. In addition, a carboxylic acid anhydride of the formula (IIIb) which is employed in excess can simultaneously function as a diluent.

The reaction temperatures can also vary within a relatively wide range in the process (a, version β) according to the invention. In general, the process is carried out at temperatures between −20° and +150° C., preferably between 0° and 100° C.

The process (a, version β) according to the invention is, in general, carried out under standard pressure.

The starting materials of the formulae (II) and (IIIb) are, in general, used in approximately equivalent amounts when the process (a, version β) according to the invention is carried out. However, it is also possible to employ the carboxylic acid anhydride in a relatively large excess.

The work-up occurs according to conventional methods.

In general, diluent and carboxylic acid anhydride which is present in excess, and the carboxylic acid produced, are removed by distillation or by washing with an organic solvent or with water.

The asymmetrical acid anhydrides which are required as reaction components in the process (a, version γ) according to the invention are clearly defined by the formula (IIIc). In this formula, $R^5$, $R^6$ and $R^7$ preferably have the meanings which have already been mentioned in connection with the description of the substances of the formula (I) according to the invention as being preferable for these radicals. R preferably represents alkyl having 1 or 2 carbon atoms or represents phenyl.

The asymmetrical acid anhydrides of the formula (IIIc) are known or can be prepared in a simple fashion according to methods which are known in principle. Thus, compounds of the formula (IIIc) are obtained by reacting carboxylic acids of the formula (III)

(III)

in which
$R^5$, $R^6$ and $R^7$ have the abovmentioned meaning, with carbonic acid ester chlorides of the formula (X),

(X)

in which
R has the abovementioned meaning,
in the presence of a diluent, such as, for example, methylene chloride, and in the presence of an acid binder, such as, for example, triethylamine, at temperatures between −20° C. and +100° C., preferably between 0° and 50° C. The asymmetrical acid anhydrides of the formula (IIIc) are, in general, not isolated in pure form, but are used further in the form which is produced, if appropriate after previous removal of diluent and/or salts.

The diluents which are also preferably suitable in the process (a, version α) can preferably be used as diluents when the process (a, version γ) according to the invention is carried out. In addition, acid anhydride of the formula (IIIc) which is employed in excess can simultaneously function as a diluent.

The reaction temperatures can also be varied within a relative wide range in the process (a, version γ) according to the invention. In general, the process is carried out at temperatures between −20° C. and +150° C., preferably between 0° and 100° C.

The process (a, version γ) according to the invention is, in general, carried out under standard pressure.

The starting materials of the formulae (II) and (IIIc) are, in general, used in approximately equivalent amounts when the process (a, version γ) according to the invention is carried out. However, it is also possible to employ the acid anhydride in a relatively large range. The work-up occurs according to conventional methods.

The compounds which are required as reaction components in the process (a, version δ) according to the invention are clearly defined by the formula (IIId). In this formula, $R^5$, $R^6$ and $R^7$ preferably have the meanings which have already been mentioned in connection with the description of the substances of the formula (I) according to the invention as being preferable for these radicals.

The compounds of the formula (IIId) are known or can be prepared in a simple fashion according to the processes which are known in principle. Thus, compounds of the formula (IIId) are obtained by reacting carboxylic acids of the formula (III),

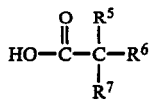
(III)

in which
R$^5$, R$^6$ and R$^7$ have the abovementioned meaning, with dicyclohexyl carbodiimide of the formula (XI),

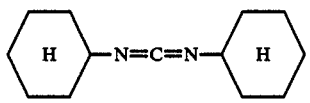
(XI)

according to conventional methods.

The diluents which are also preferably suitable in the process (a, version α) are preferably used as diluents when the process (a, version δ) according to the invention is carried out.

The reaction temperatures can also be varied within a relatively wide range in the process (a, version δ) according to the invention. In general, the process is carried out at temperatures between −20° C. and +150° C., preferably between 0° and 100° C.

The process (a, version δ) according to the invention is, in general, carried out under standard pressure.

The starting materials of the formulae (II) and (IIId) are, in general, used in approximately equivalent amounts when the process (a, version δ) according to the invention is carried out. The work-up occurs according to conventional methods.

The pyrimidine derivatives of the formula (IV) which are required as starting materials in the process (b) according to the invention have already been dealt with in connection with the description of the process (c).

The acylaniline derivatives which are furthermore required as starting materials in the process (b) according to the invention are clearly defined by the formula (V). In this formula, R$^4$, R$^5$, R$^6$, R$^7$ and n preferably have the meanings which have already been mentioned in connection with the description of the substances of the formula (I) as being preferable for these radicals and for this index respectively.

The compounds of the formula (V) are known or can be prepared in a simple fashion according to methods which are known in principle. Thus, acylaniline derivatives of the formula (V) are obtained, for example, by reacting 4-amino-thiophenols of the formula (VI),

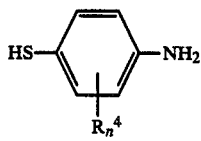
(VI)

in which
R$^4$ and n have the abovementioned meaning, with acid halides of the formula

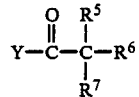
(IIIa)

in which
R$^5$, R$^6$, R$^7$ and Y have the abovementioned meaning, if appropriate in the presence of a diluent and if appropriate in the presence of an acid binder. The reaction conditions here correspond to those which are also used when the process (a, version α) is carried out.

All conventional acid acceptors can be employed as acid binders when the process (b) according to the invention is carried out. Alkali metal and alkaline earth metal oxides, hydroxides and carbonates, such as sodium hydroxide, potassium hydroxide, magnesium oxide, calcium oxide, sodium carbonate, potassium carbonate and calcium carbonate, furthermore alkali metal and alkaline earth metal amides and hydrides, such as sodium amide, sodium hydride and calcium hydride, and, in addition, also alkali metal alcoholates, such as sodium methylate, sodium ethylene and potassium tert.-butylate, can preferably be used.

All conventional inert organic solvents can be employed as diluents in the process (b) according to the invention. Hydrocarbons, such as toluene and xylene, furthermore ethers, such as dibutyl ether, tetrahydrofuran, dioxane, glycol dimethyl ether and diglycol dimethyl ether, in addition nitriles, such as acetonitrile and propionitrile, and furthermore polar solvents, such as nitrobenzene, dimethyl sulphoxide, sulpholane, dimethylformamide and N-methyl-pyrrolidone, can preferably be used.

The reaction temperatures can be varied within a relatively wide range when the process (b) according to the invention is carried out. In general, the process is carried out at temperatures between 0° and 200° C., preferably between 50° and 150° C.

The process (b) according to the invention is, in general, carried out under standard pressure.

The reaction components of the formulae (IV) and (V) are, in general, employed in approximately equimolar amounts when the process (b) according to the invention is carried out.

However, it is also possible to use either component in a relatively large excess. In addition, an equimolar amount of acid binder is also employed in general. However, it can also be advantageous to add the acid binder in an excess of up to one molar. In detail, the acid binder is added to a mixture of the reaction components in a suitable diluent. However, a procedure can also be followed where a salt is initially generated from the acylaniline derivative of the formula (V) and this salt is then reacted with a pyrimidine derivative of the formula (IV). It is furthermore also possible initially to prepare a salt separately from the acylaniline derivative of the formula (V) with an acid binder, then to isolate this salt and subsequently to react it with a pyrimidine derivative of the formula (IV) in the presence of a suitable diluent without further addition an acid binder. The work-up occurs according to conventional methods in each case.

The active compounds according to the invention can be used as defoliants, desiccants, agents for destroying broad-leaved plants and, especially, as weed-killers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papavar and Centaurea.

Dicotyledon cultures of the genera: Gossypium, Glycine, Beta, Daucus, Phaseolus, Pismum, Solanum, Linium, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodum, Monochoria, Fimbristylis, Sagittaria, Eleocharis, Scirpus, Paspalum, Ischaemum, Sphenoclea, Dactyloctenium, Agrostics, Alopercurus and Apera.

Monocotyledon cultures of the genera: Oryza, Zea, Triticum, Hordeum, Avena, Secale, Sorghum, Phanicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are especially suitable for selective combating of monocotyledon and dicotyledon weeds in monocotyledon cultures, such as, for example, corn and cereals.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention are especially advantageous for combating *Pyricularia oryzae* in rice, botrytis and bean rust.

In addition, the substances according to the invention also distinguish themselves by an insecticidal activity. They have a good root-systemic activity here.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents' and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5(4H)-one, 4-amino-6-t-butyl-3-ethylthio-1,2,4-triazin-5(4H)-one, 2-chloro-4-ethylamino-6-isopropyl-amino-1,3,5-triazine, 2-chloro-4-ethylamino-6-(3-cyanopropylamino)-1,3,5-triazine, the R-enantiomer of (trimethylsilyl)-methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, methyl-2-[4-(2,4-dichlorophenoxy)-phenoxy]-propionate, 4-chloro-2-methylphenoxy acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can, when used as herbicides, be applied either before or after emergence of the plants. They can also be incorporated into the soil before sowing.

The amount of active compound used can vary within a substantial range when the substances according to the invention are used as herbicides. It depends essentially on the nature of the desired effect. In general, the amounts used are between 0.01 and 10 kg of active compound per hectare of soil surface, preferably between 0.05 and 5 kg per ha.

The amount used can also be varied within a substantial range, depending on the type of application, when the substances according to the invention are used as fungicides. Thus, the active compound concentrations are, in general, between 1 and 0.0001% by weight, preferably between 0.5 and 0.001% by weight, in the use forms for treatment of plant parts. For treatment of seed, amounts of active compound from 0.001 to 50 g, preferably 0.01 to 10 g, are required per kg of seed. For treatment of the soil, active compound concentrations of 0.00001 to 0.1% by weight, preferably 0.0001 to 0.02% by weight, are required at the place of action.

The preparation and use of the active compounds according to the invention are apparent from the examples which follow.

PREPARATION EXAMPLES

EXAMPLE 1

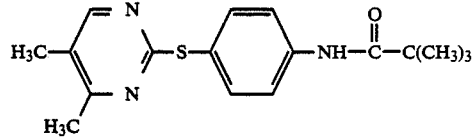

23.1 g (0.1 mol) of 2-(4-amino-phenyl-mercapto)-4,5-dimethyl-pyrimidine are dissolved in 150 ml of tetrahydrofuran. 10.1 g (0.1 mol) of triethylamine are added to this solution, and 12.05 g (0.1 mol) of pivalic chloride are subsequently added dropwise at 15°-20° C. The mixture is stirred for 2 hours at room temperature and then stirred into 1 l of water. The crystals which precipitate are filtered off under suction, washed with water and dried in air.

29.0 g (92% of theory) of 2-(4-pivaloylaminophenyl-mercapto)-4,5-dimethylpyrimidine with melting point 156°-158° C. (recrystallization from petroleum ether) are obtained.

The compounds of the formula (I) the formulae of which are listed in Table 2 below are obtained according to the method stated in the preceding example and according to the methods in the description:

TABLE 2

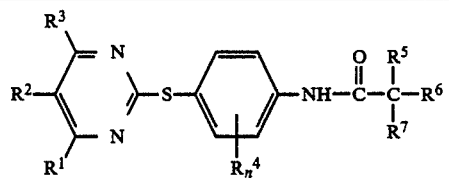

(I)

| Example | $R^1$ | $R^2$ | $R^3$ | $R^4$ | $R^5$ | $R^6$ | $R^7$ | melting point (°C.) |
|---|---|---|---|---|---|---|---|---|
| 2 | CH$_3$ | CH$_3$ | H | — | CH$_2$Cl | CH$_3$ | CH$_3$ | 122–124 |
| 3 | CH$_3$ | CH$_3$ | H | — | C$_3$H$_7$ | CH$_3$ | CH$_3$ | 114–116 |
| 4 | CH$_3$ | CH$_3$ | H | — | CH$_3$ | —(CH$_2$)$_5$— | | 122–124 |
| 5 | C$_2$H$_5$ | CH$_3$ | H | — | CH$_3$ | CH$_3$ | CH$_3$ | 146–147 |
| 6 | CH$_3$ | Cl | CH$_3$ | — | CH$_3$ | CH$_3$ | CH$_3$ | 190–192 |
| 7 | CH$_3$ | CH$_3$ | CH$_3$ | — | CH$_3$ | CH$_3$ | CH$_3$ | 216–218 |
| 8 | CH$_3$ | CH$_3$ | CH$_3$ | — | CH$_2$Cl | CH$_3$ | CH$_3$ | 200–202 |
| 9 | CH$_3$ | C$_2$H$_5$ | CH$_3$ | — | CH$_3$ | CH$_3$ | CH$_3$ | 188–190 |
| 10 | CH$_3$ | C$_2$H$_5$ | CH$_3$ | — | CH$_2$Cl | CH$_3$ | CH$_3$ | 140–141 |
| 11 | CH$_3$ | C$_2$H$_5$ | CH$_3$ | — | CH$_3$ | —(CH$_2$)$_5$— | | 150–152 |
| 12 | CH$_3$ | CH$_3$ | H | — | C$_2$H$_5$ | C$_2$H$_5$ | H | 171–173 |
| 13 | CH$_3$ | CH$_3$ | H | — | CN | CH$_3$ | CH$_3$ | 156–158 |
| 14 | CH$_3$ | CH$_3$ | H | — | C$_2$H$_5$ | CH$_3$ | CH$_3$ | 121–123 |
| 15 | CH$_3$ | CH$_3$ | H | — | CH(CH$_3$)$_2$ | CH$_3$ | CH$_3$ | 106–108 |

TABLE 2-continued (I) structure shown with $R^1, R^2, R^3$ on pyrimidine ring, S linkage to phenyl ring bearing $R^4_n$ and NH-C(=O)-C($R^5$)($R^6$)$R^7$ group.

| Example | $R^1$ | $R^2$ | $R^3$ | $R^4$ | $R^5$ | $R^6$ | $R^7$ | melting point (°C.) |
|---|---|---|---|---|---|---|---|---|
| 16 | $CH_3$ | $CH_3$ | H | — | $CH_3$ | —$CH_2$—O—$CH_2$— | | 147–149 |
| 17 | $CH_3$ | $CH_3$ | H | — | $CH_3$ | —O—$(CH_2)_4$— | | 106–108 |
| 18 | $CH_3$ | $CH_3$ | H | 3-Cl | $CH_3$ | $CH_3$ | $CH_3$ | 172–174 |
| 19 | $CH_3$ | $CH_3$ | H | 3-Cl | $CH_2Cl$ | $CH_3$ | $CH_3$ | 161–163 |
| 20 | $CH_3$ | $CH_3$ | H | 3-Cl | $C_2H_5$ | $CH_3$ | $CH_3$ | 124–125 |
| 21 | $CH_3$ | $CH_3$ | H | 3-Cl | $CH_3$ | —$(CH_2)_5$— | | 142–144 |
| 22 | $CH_3$ | $CH_3$ | H | 3-$OCH_3$ | $CH_3$ | $CH_3$ | $CH_3$ | 150–152 |
| 23 | $CH_3$ | $CH_3$ | H | 3-$OCH_3$ | $CH(CH_3)_2$ | $CH_3$ | $CH_3$ | 129–131 |
| 24 | $CH_3$ | $C_2H_5$ | H | — | $CH_3$ | $CH_3$ | $CH_3$ | 128–130 |
| 25 | $CH_3$ | $C_2H_5$ | H | — | $C_2H_5$ | $CH_3$ | $CH_3$ | 124–126 |
| 26 | $CH_3$ | Cl | $CH_3$ | — | $CH_2Cl$ | $CH_3$ | $CH_3$ | 185–187 |
| 27 | $CH_3$ | Cl | $CH_3$ | — | $C_2H_5$ | $CH_3$ | $CH_3$ | 180–182 |
| 28 | $CH_3$ | Cl | $CH_3$ | — | $C_3H_7$ | $CH_3$ | | 148–150 |
| 29 | $CH_3$ | Cl | $CH_3$ | — | $CH_3$ | —$(CH_2)_5$— | | 150–151 |
| 30 | $CH_3$ | Cl | $CH_3$ | 3-Cl | $CH_3$ | $CH_3$ | $CH_3$ | 208–209 |

PREPARATION OF STARTING COMPOUNDS

EXAMPLE VII-1

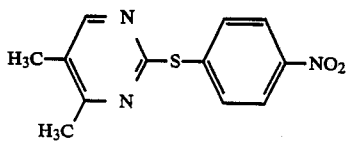

88.25 g (0.5 mol) of 4,5-dimethyl-2-mercapto-pyrimidine hydrochloride are suspended in 1 l of sulpholane. 70 g (1.25 mol) of powdered potassium hydroxide are introduced in portions with stirring at room temperature. The mixture is stirred for 30 minutes, and 79 g (0.5 mol) of 4-chloro-nitro-benzene are then added. The mixture is stirred for 1 hour at room temperature and then heated at 120°–130° C. for 3 hours. After cooling, the reaction mixture is poured into 3 l of ice water.

The crystals which precipitate are filtered off under suction and dried in air.

112 g (85.8% of theory) of 2-(4-nitro-phenyl-mercapto)-4,5-dimethyl-pyrimidine with melting point 92°–94° C. (recrystallization from methanol) are obtained.

The following are obtained in a corresponding fashion:

EXAMPLE VII-2

2-(4-Nitro-phenyl-mercapto)-4-ethyl-5-methyl-pyrimidine:

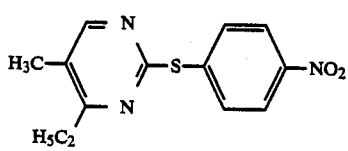

Melting point: 70°–72° C. (recrystallization from ethanol).

EXAMPLE VII-3

2-(4-Nitro-phenyl-mercapto)-4,5,6-trimethyl-pyrimidine:

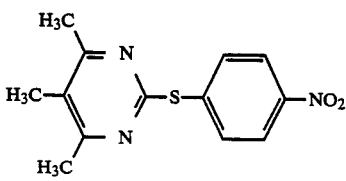

EXAMPLE VII-4

2-(4-Nitro-phenyl-mercapto)-5-ethyl-4,6-dimethyl-pyrimidine:

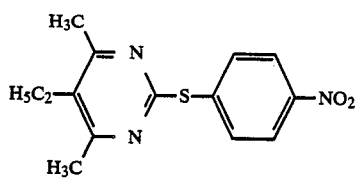

Melting point: 82°–84° C. (recrystallization from toluene).

EXAMPLE VII-5

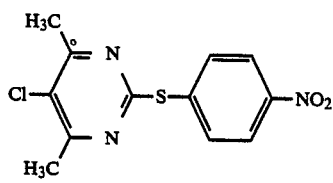

26.1 g (0.1 mol) of 2-(4-nitro-phenyl-mercapto)-4,6-dimethyl-pyrimidine are suspended in 200 ml of tetrachloromethane. 14.9 g (1.1 moles) of sulphuryl chloride are added dropwise to this suspension at room temperature. The mixture is refluxed for 3 hours and filtered while hot, the solution is concentrated in vacuo and the residue is recrystallized from petroleum ether.

15 g (50.8% of theory) of 2-(4-nitrophenyl-mercapto)-5-chloro-4,6-dimethyl-pyrimidine with melting point 110° C. are obtained.

EXAMPLE II-1

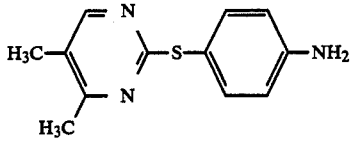

Process (d)

78.3 g (0.3 mol) of 2-(4-nitro-phenyl-mercapto)-4,5-dimethyl-pyrimidine are hydrogenated to exhaustion in 400 ml of dioxane with addition of 15 g of Raney nickel at 20°–50° C. The catalyst is filtered off under suction and the solution is concentrated in vacuo.

A practically quantitative yield of 2-(4-amino-phenyl-mercapto)-4,5-dimethyl-pyrimidine with melting point 126°–128° C. (recrystallization from toluene) remains.

The following are obtained in a corresponding fashion:

EXAMPLE II-2

2-(4-Amino-phenyl-mercapto)-4-ethyl-5-methyl-pyrimidine:

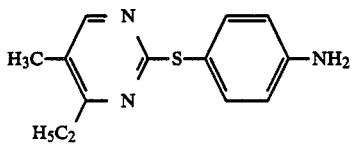

Melting point: 88°–90° C. (recrystallization from petroleum ether).

EXAMPLE II-3

2-(4-Amino-phenyl-mercapto)-4,5,6-trimethyl-pyrimidine:

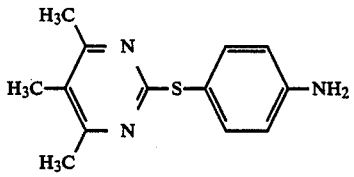

Melting point: 152°–154° C. (recrystallization from toluene).

EXAMPLE II-4

2-(4-Amino-phenyl-mercapto)-5-ethyl-4,6-dimethyl-pyrimidine

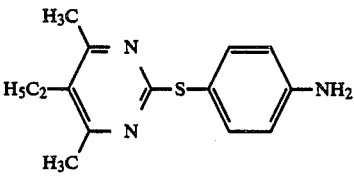

Melting point: 157°–159° C. (recrystallization from toluene).

EXAMPLE II-5

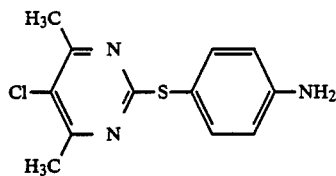

Process (c)

25 g (0.2 mol) of 4-amino-thiophenol are dissolved in 150 ml of N-methyl-pyrrolidone. 12.3 g (0.22 mol) of powdered potassium hydroxide and subsequently 35.4 g (0.2 mol) of 2,5-dichloro-4,6-dimethyl-pyrimidine are added to the solution. This mixture is warmed at 120° C. for 5 hours and stirred into 1 liter of water after cooling. The crystals are filtered off under suction, washed with water and dried.

46.2 g (87% of theory) of 2-(4-amino-phenyl-mercapto)-5-chloro-4,6-dimethyl-pyrimidine with melting point of 160°–161° C. are obtained.

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

In this test, the compounds according to Examples 1, 3, 4, 6, 10, 13, 14, 15, 18, 19, 20 and 25 exhibit very good herbicidal activity for the selective combating of monocotyledon and dicotyledon weeds, such as, for example, Setaria, Amaranthus and Chenopodium, in monocotyledon crops, such as wheat and corn.

It is understood that the specification and examples are illustrative but not limitative of the present invention and that other embodiments within the spirit and scope of the invention will suggest themselves to those skilled in the art.

What is claimed is:

1. A pyrimidylmercaptoacylanilide of the formula

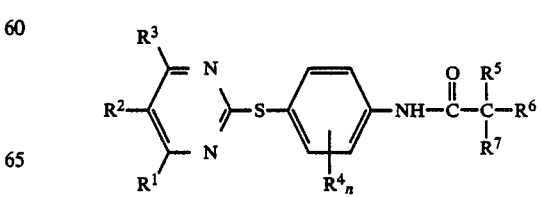

in which $R^1$ represents methyl or ethyl, $R^2$ represents halogen, methyl or ethyl, $R^3$ represents hydrogen or methyl, $R^4$ represents halogen, methyl or methoxy, n represents 0, 1 or 2, $R^5$ represents hydrogen, halogen, cyano, alkyl having 1 to 6 carbon atoms which is unsubstituted or substituted by fluorine, chlorine, bromine or alkoxy having 1 to 4 carbon atoms, phenyl which is unsubstituted or substituted by fluorine, chlorine, bromine, trifluoromethyl, methoxy or methyl, benzyl which is unsubstituted or substituted by fluorine, chlorine, bromine, trifluoromethyl, methoxy or methyl, or the $-OR^8$ or $-SO_m-R^8$ radical, where $R^8$ represents alkyl having 1 to 6 carbon atoms unsubstituted or substituted by fluorine, chlorine or bromine, or phenyl which is unsubstituted or substituted by fluorine, chlorine, bromine or alkyl having 1 to 4 carbon atoms and m represents 0, 1 or 2, and $R^6$ and $R^7$, independently of one another, represent halogen or alkyl having 1 to 6 carbon atoms unsubstituted or substituted by fluorine, chlorine or bromine, or $R^5$ and $R^6$, together with the neighboring carbon atom, represent a carbocyclic ring or a ring which can also contain oxygen in the ring in addition to carbon atoms, which has 3 to 8 ring members, and which is unsubstituted or substituted by fluorine, chlorine or alkyl having 1 to 4 carbon atoms or $R^6$ and $R^7$, together with the neighboring carbon atom, represent a carbocyclic ring or a ring which can contain oxygen in the ring in addition to carbon atoms, which has 3 to 8 ring carbon atoms, and which is unsubstituted or substituted by fluorine, chlorine or alkyl having 1 to 4 carbon atoms.

2. A pyrimidylmercapto-acylanilide according to claim 1, in which $R^1$ represents methyl or ethyl, $R^2$ represents fluorine, chlorine, bromine, methyl or ethyl, $R^3$ represents hydrogen or methyl, $R^4$ represents fluorine, chlorine, bromine, methyl or methoxy, n represents 0 or 1, $R^5$ represents hydrogen, fluorine, chlorine, bromine, cyano, alkyl, having 1 to 4 carbon atoms, which is unsubstituted or substituted by fluorine, chlorine, bromine or alkoxy having 1 to 4 carbon atoms, phenyl chlorine, bromine, trifluoromethyl, methoxy or methyl, benzyl which is unsubstituted or substituted by fluorine, chlorine, bromine, trifluoromethyl, methoxy or methyl, or represents the $-OR^8$ or $-SO_m-R^8$ radical, where $R^8$ represents alkyl, having 1 to 4 carbon atoms, which is unsubstituted or substituted by fluorine, chlorine or bromine, or phenyl which is unsubstituted or substituted by fluorine, chlorine, bromine or alkyl having 1 to 4 carbon atoms and m represents 0, 1 or 2, $R^6$ and $R^7$, independently of one another, represent fluorine, chlorine, bromine or alkyl having 1 to 4 carbon atoms, which is unsubstituted or substituted by fluorine, chlorine or bromine or $R^5$ and $R^6$, together with the neighboring carbon atom, represent a carbocyclic ring or a ring which can also contain oxygen in the ring in addition to carbon atoms, which has 3 to 7 ring atoms and which is unsubstituted or substituted by fluorine, chlorine or alkyl having 1 to 4 carbon atoms or $R^6$ and $R^7$, independently with the neighbouring carbon atom, represent a carbocyclic ring, which has 3 to 7 ring atoms and which is unsubstituted or substituted by fluorine, chlorine or alkyl having 1 to 4 carbon atoms.

3. A pyrimidylmercapto-acylanilide according to claim 1, in which $R^1$ represents methyl or ethyl, $R^2$ represents fluorine, chlorine, methyl or ethyl, $R^3$ represents hydrogen or methyl, $R^4$ represents fluorine, chlorine, methyl or methoxy, n represents 0 or 1, $R^5$ represents fluorine, chlorine, bromine, cyano, alkyl, having 1 to 4 carbon atoms, which is unsubstituted or singly to quintuply substituted by fluorine, chlorine, methoxy or ethoxy, phenyl which is optionally singly to triply substituted by fluorine, chlorine or methyl, benzyl which is unsubstituted or singly to quintuply substituted by fluorine, chlorine or methyl or the $-OR^8$ or $-SO_m-R^8$ radical, where $R^8$ represents alkyl, having 1 to 4 carbon atoms, which is unsubstituted or singly to quintuply substituted by fluorine or chlorine, or represents phenyl which is unsubstituted or singly to quintuply substituted by fluorine, chlorine or alkyl having 1 to 4 carbon atoms and m represents 0, 1 or 2, $R^6$ and $R^7$, independently of one another, represent fluorine, chlorine or alkyl, having 1 to 4 carbon atoms, which is unsubstituted or singly to quintuply substituted by fluorine or chlorine or $R^5$ and $R^6$, together with the neighboring carbon atom, represent a carbocyclic ring or a ring which can also contain oxygen in the ring in addition to carbon atoms, which has 3 to 7 ring atoms, and which is unsubstituted or singly to quintuply identically or differently substituted by fluorine, chlorine, methyl, ethyl, n-propyl, iso-propyl, n-butyl, iso-butyl, sec.-butyl and tert.-butyl, or $R^6$ and $R^7$, together with the neighbouring carbon atom, represent a carbocyclic ring which has 3 to 7 ring atoms and which is unsubstituted or singly to quintuply identically or differently substituted by fluorine, chlorine, methyl, ethyl, n-propyl, iso-propyl, n-butyl, iso-butyl, sec.-butyl or tert.-butyl.

4. A compound according to claim 1, wherein such compound is 2-(4-pivaloylaminophenylmercapto-4,5-dimethylpyrimidine of the formula

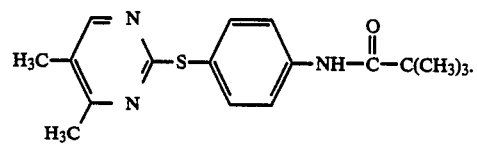

5. A compound according to claim 1, wherein such compound is 2-([2,2-dimethyl-butyryl]-aminophenylmercapto)-4,5-dimethylpyrimidine of the formula

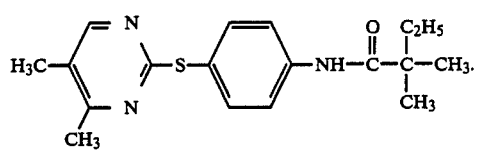

6. A compound according to claim 1, wherein such compound is 2-([2,2,3-trimethyl-butyryl]-aminophenyl-mercapto)-4,5-dimethylpyrimidine of the formula

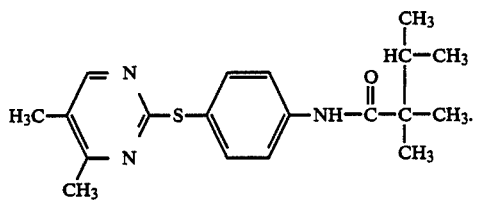

7. A compound according to claim 1, wherein such compound is 2-([2-(2-methyl)-tetrahydropyranoyl]-aminophenylmercapto)-4,5-dimethyl-pyrimidine of the formula

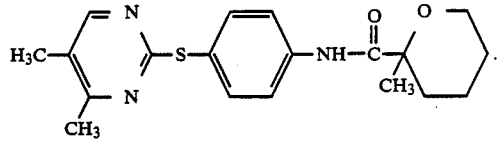

8. A compound according to claim 1, wherein such compound is 2-([2,2-dimethyl-propionyl]-aminophenylmercapto)-4-methyl-5-ethyl-pyrimidine of the formula

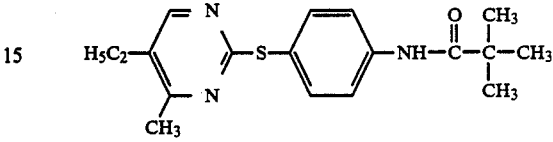

9. A herbicidal composition comprising an amount effective therefor for a pyrimidylmercapto-acylanilide according to claim 1 and a diluent.

10. A method of combating unwanted vegetation which comprises applying thereto or to a locus from which is is desired to exclude such vegetation a herbicidally effective amount of pyrimidylmercapto-acylanilide according to claim 1.

11. A method according to claim 10 wherein such compound is 2-(4-pivaloylaminophenylmercapto)-4,5-dimethylpyrimidine, 2-([2,2-dimethyl-butyryl]-aminophenylmercapto)-4,5-dimethylpyrimidine, 2-([2,23-trimethyl-butyryl]-aminophenylmercapto)-4,5-dimethylpyrimidine, 2-([2-(2-methyl)-tetrahydropyranoyl]-aminophenylmercapto)-4,5-dimethyl-pyrimidine or 2-([2,2-dimethyl-propionyl]-aminophenylmercapto)-4-methyl-5-ethyl-pyrimidine.

* * * * *

UNITED STATES PATENT AND TRADEMARK OFFICE
CERTIFICATE OF CORRECTION

PATENT NO. : 4,797,146
DATED : Jan. 10, 1989
INVENTOR(S) : Sasse et al.

It is certified that error appears in the above-identified patent and that said Letters Patent is hereby corrected as shown below:

| | |
|---|---|
| Title Page, under U.S. Patent Documents", line 1 | Correct date --12/1986-- |
| Title Page, last line | Delete "12 Claims" and substitute --11 Claims-- |
| Col. 17, line 19 | Correct spelling of --Linum-- |
| Col. 17, line 29 | Correct spelling of --Panicum-- |
| Col. 25, line 15 | Delete "unsubstituted or" after "atoms" |
| Col. 25, line 22 | Delete "unsubstituted or" after "atoms" |
| Col. 25, line 50 | Insert --which is unsubstituted or substituted by fluorine-- after "phenyl" |
| Col. 26, line 20 | Delete "optionally" and insert --unsubstituted or-- after "is" |

Signed and Sealed this

Twenty-first Day of November, 1989

Attest:

JEFFREY M. SAMUELS

Attesting Officer     Acting Commissioner of Patents and Trademarks